United States Patent [19]

Hayes et al.

[11] Patent Number: 5,298,205
[45] Date of Patent: Mar. 29, 1994

[54] CERAMIC FILTER PROCESS

[75] Inventors: Kevin G. Hayes; Peter A. Roberts, both of Alfred, N.Y.

[73] Assignee: PolyCeramics, Inc., Alfred, N.Y.

[21] Appl. No.: 936,762

[22] Filed: Aug. 27, 1992

Related U.S. Application Data

[63] Continuation-in-part of Ser. No. 881,056, May 11, 1992.

[51] Int. Cl.⁵ ............................................. C04B 38/06
[52] U.S. Cl. .......................................... 264/25; 264/44; 264/59; 264/63; 264/67
[58] Field of Search ................. 264/25, 44, 59, 63, 264/67; 106/149

[56] References Cited

U.S. PATENT DOCUMENTS 3,090,094  5/1963  Schwartzwalder .............. 264/44
3,111,396  11/1963  Ball et al. ......................... 264/44

OTHER PUBLICATIONS

The Condensed Chemical Dictionary, 6th Edition, 1961 Reinhold Publ. Corp., New York, p. 540.

Primary Examiner—James Derrington
Attorney, Agent, or Firm—Howard J. Greenwald

[57] ABSTRACT

A process for preparing a porous ceramic material, is disclosed. The process uses an organic sponge material, and a ceramic slurry. The ceramic slurry contains liquid, gluten, and ceramic material.

In the first step of the process, the ceramic slurry is applied to the sponge in order to substantially saturate it with slurry. Thereafter, the saturated sponge is dehydrated until it contains less than about 5.0 weight percent of liquid. The dehydrated sponge is then fired at a temperature of from about 1,100 to about 3,500 degrees Fahrenheit.

17 Claims, 8 Drawing Sheets

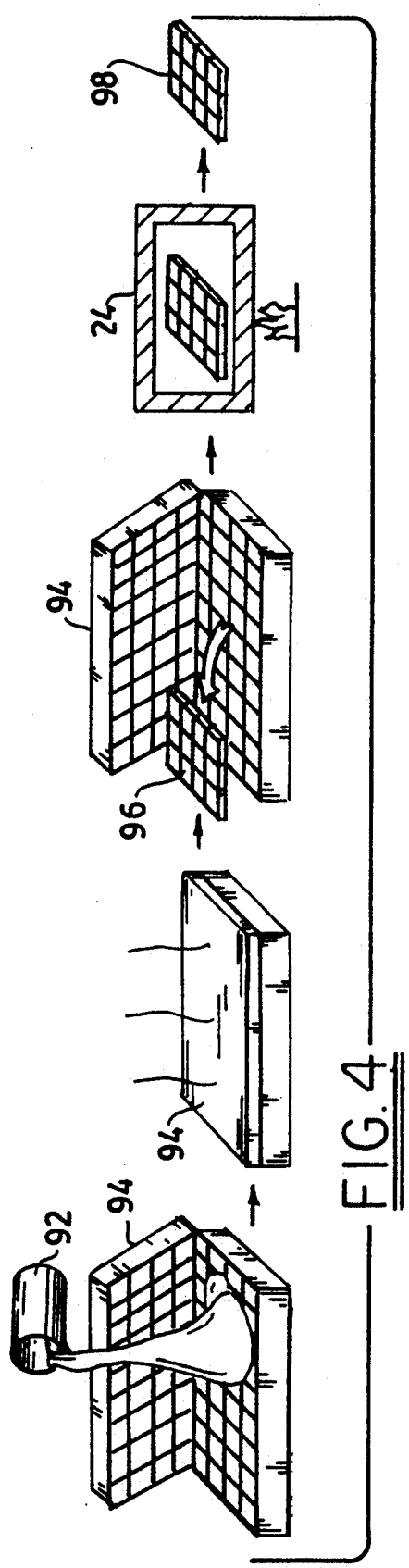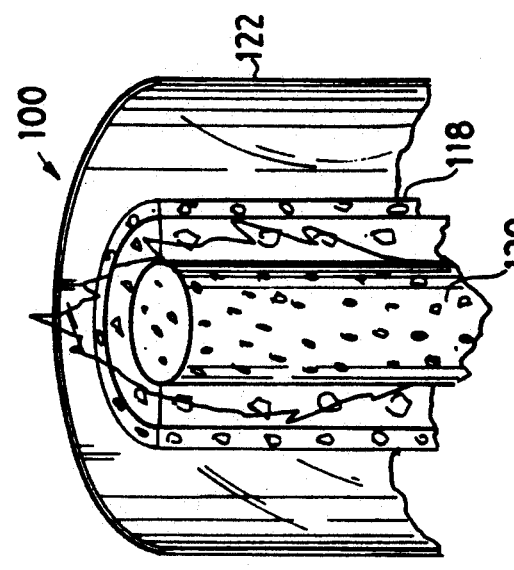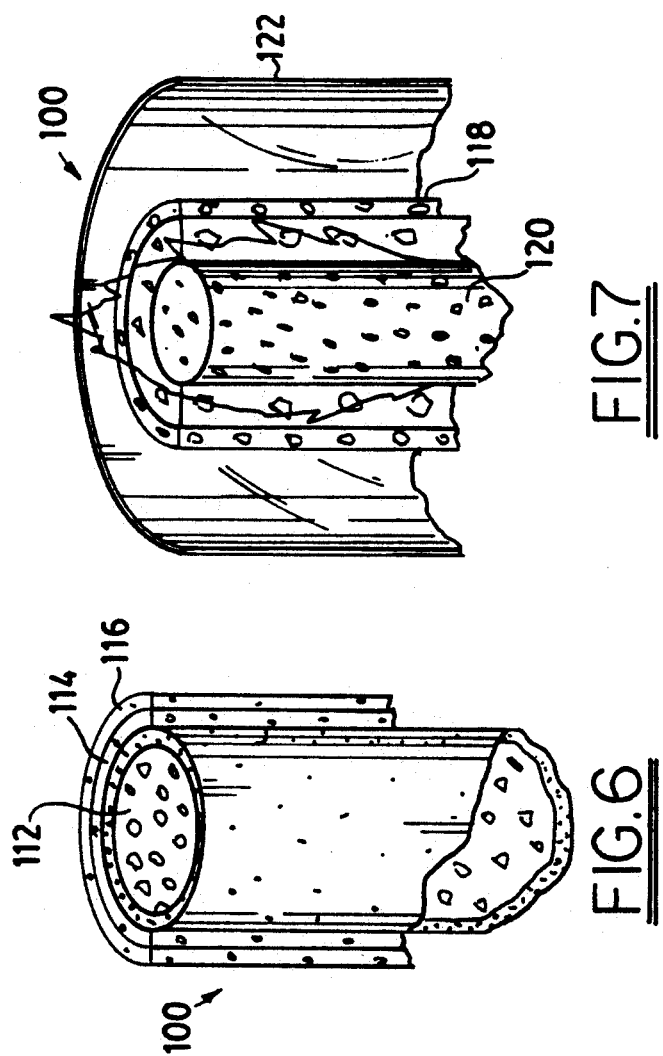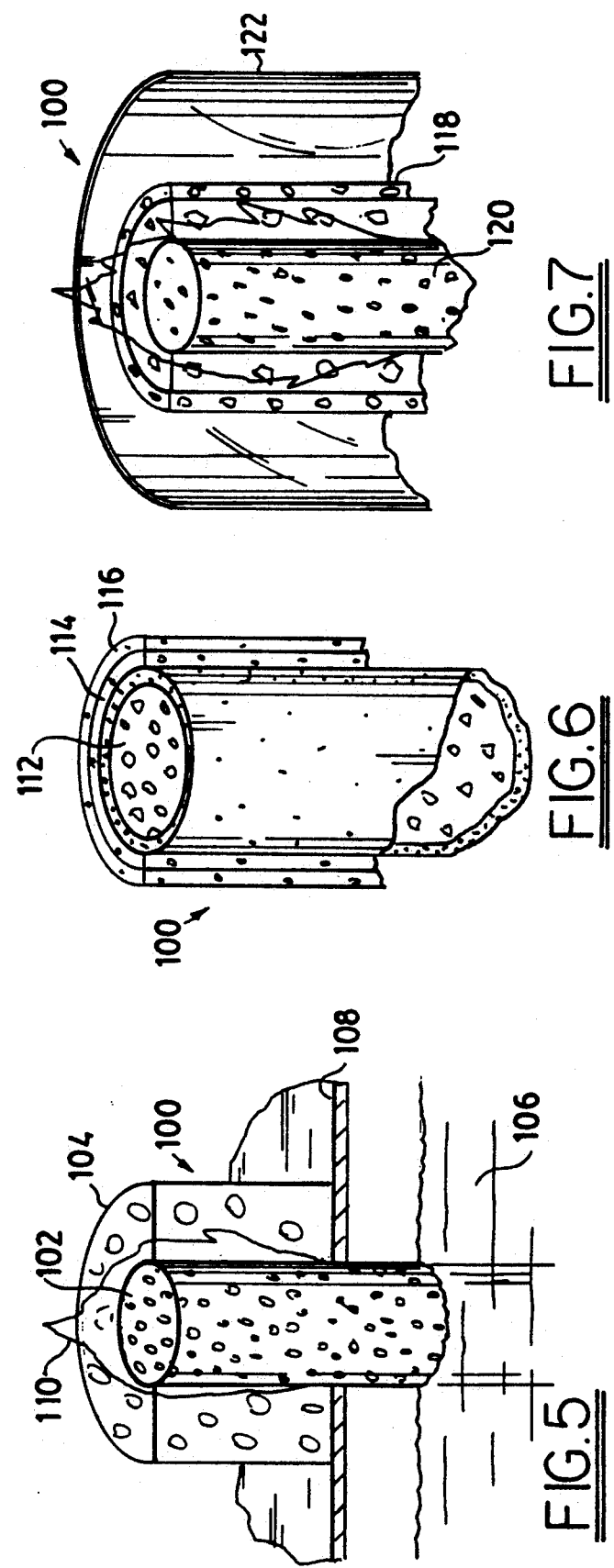

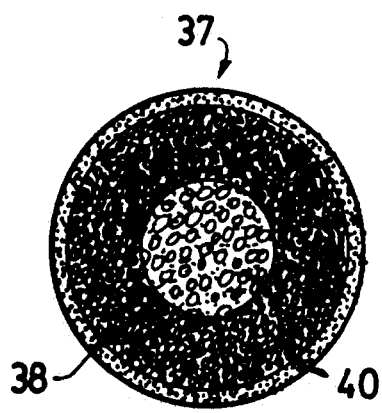
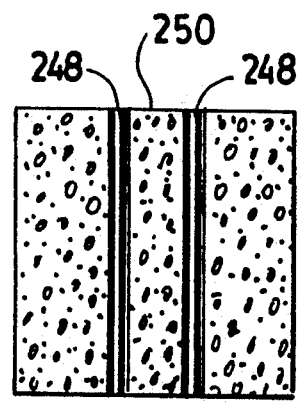
FIG.24    FIG.25
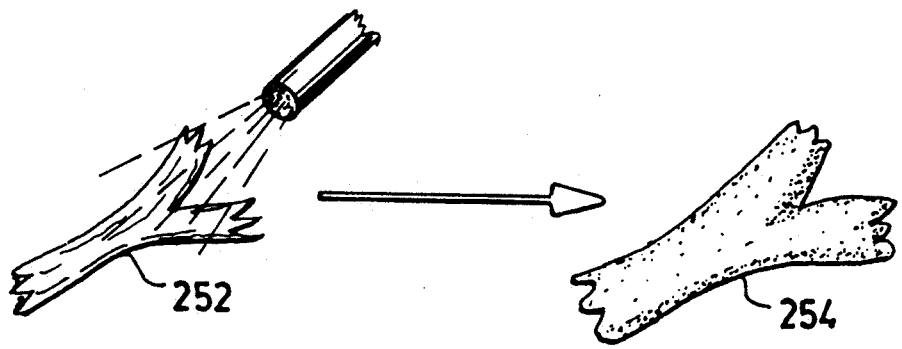
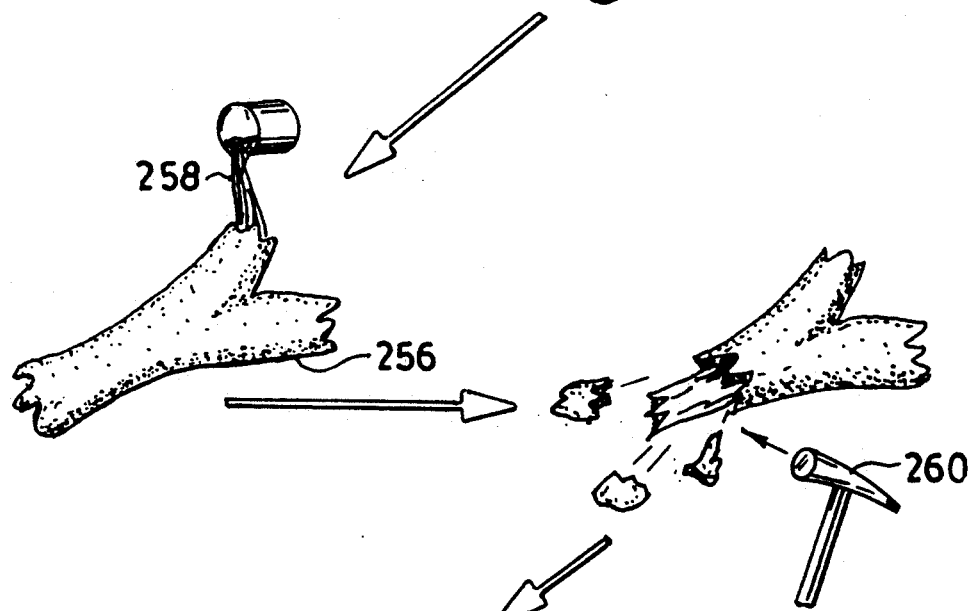
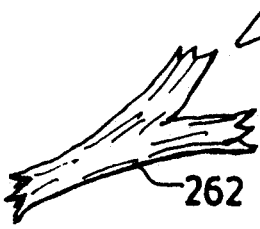
FIG.26

CERAMIC FILTER PROCESS

CROSS-REFERENCE TO RELATED PATENT APPLICATION

This is a continuation-in-part of applicants, copending patent application U.S. Ser. No. 07/881,056, filed on May 11, 1992.

FIELD OF THE INVENTION

A process for making a ceramic filter body from a batch containing gluten and ceramic material is disclosed.

BACKGROUND OF THE INVENTION

Processes are known for making shaped ceramic materials using natural objects as a mold. However, when such processes are used to attempt to make complicated shapes, many problems often arise. In the first place, because of the high shrinkage of most ceramic materials, cracking of the ceramic body often occurs upon drying the green body and/or upon firing it. In the second place, inasmuch as moisture often is present in the pores of the green body, the evaporation of this moisture during drying or firing often causes cracking of the body.

It is an object of this invention to provide a ceramic batch material which is uniquely suitable for forming complicated shapes.

It is another object of this invention to provide a ceramic batch material which will expand during thermal processing and will assume the shape of a mold in which it is situated.

It is another object of this invention to provide an intermediate material which is comprised of the ceramic batch material and which can be used to form a fired, shaped body.

It is another object of this invention to provide a multiplicity of objects and compositions which can be made from the ceramic batch material discussed above.

It is another object of this invention to provide a process for growing plants with some of the fired objects of this invention.

SUMMARY OF THE INVENTION

In accordance with this invention, there is provided a process for making a ceramic body. In the first step of this process, a composition comprised of gluten and ceramic material is provided. In the second step of this process, an open-celled organic structure is filled with the composition. In the third step of the process, the filled organic structure is heated and, thereafter, fired.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 4 is a flow diagram illustrating one preferred forming process of the invention;

FIGS. 5, 6, 7, and 8, are views illustrating a ceramic wick comprised of one of the compositions of this invention as well as the use of such wick;

FIG. 24 is a sectional view of one ceramic body made by the process of this invention;

FIGS. 25 and 26 illustrate other forming processes and

DESCRIPTION OF THE PREFERRED EMBODIMENT

Figure 1:
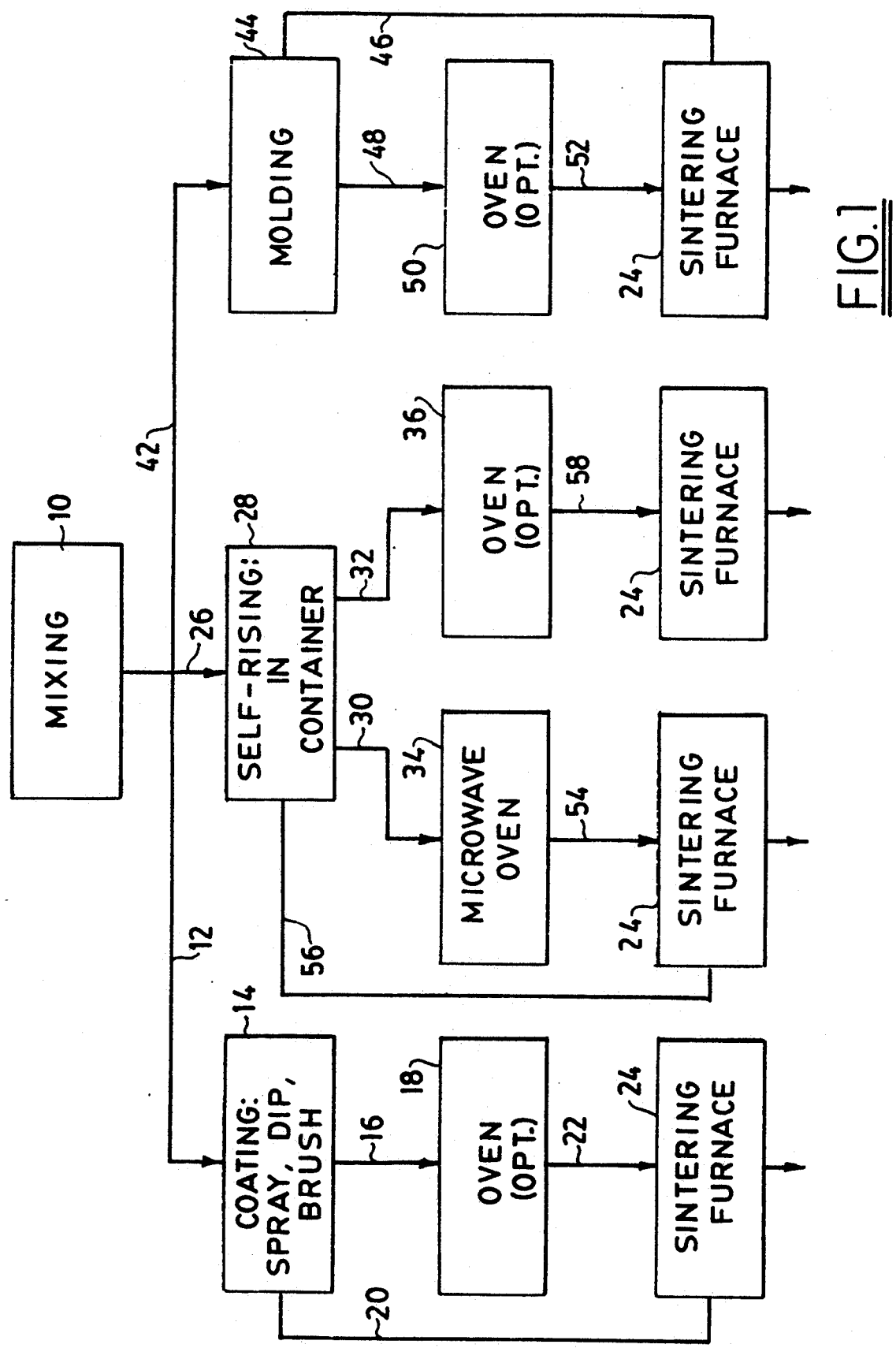
FIG. 1 is a flow diagram illustrating several preferred processes of applicants' invention.

The present invention involves the discovery that a ceramic composition comprised of at least 10 weight percent of ceramic material and an effective amount of gluten is a surprisingly effective product.

The ceramic composition of this invention is preferably comprised of at least about 10 weight percent of ceramic material, by combined weight of ceramic material and gluten. As is known to those skilled in the art, many materials contain both gluten and other organic materials; thus, corn meal contains both corn gluten, fiber, fat, and other materials. When, for example, the concentration of ceramic material in a mixture comprised of corn meal is to be calculated, one first determines the concentration of the corn gluten in the corn meal.

As is known to those skilled in the art, gluten is comprised of at least 85 weight percent of protein. The proteins in gluten include gliadin, glutenin, globulin, and albumin.

Gliadin is a prolamin (a simple vegetable protein) which is described, e.g., in U.S. Pat. Nos. 4,935,257 and 4,911,942, the disclosure of each of which is hereby incorporated by reference into this specification. Wheat gliadin contains about 52.7 percent of carbon, about 17.7 percent of nitrogen, about 21.7 percent of oxygen, about 6.9 percent of hydrogen, and about 1.0 percent of sulfur; and it is composed of 18 amino acids, about 40 weight percent being glutamic acid.

Glutenin is one of the proteins present in wheat flour in substantial percentage; it is composed of 18 amino acids. Glutenin is described in U.S. Pat. Nos. 3,651,768, 4,911,942, and 4,935,257, the disclosure of each of which is hereby incorporated by reference into this specification.

Globulin is a general name for a member of a heterogeneous group of serum proteins precipitated by 50 percent saturated ammonium sulfate, and thus differing from albumin, the protein present in greatest concentration in normal serum. Globulin generally may be coagulated by heat, is insoluble in water, and is soluble in dilute solutions of salts, strong acids, and strong alkalies. Globulin is described, e.g., in U.S. Pat. Nos. 4,670,544, 4,482,483, and 3,985,506, the disclosure of each of which is hereby incorporated by reference into this specification.

Albumin is a widely-occurring water-soluble protein which can be readily coagulated by heat and hydrolyzes to alpha-amino acids or their derivatives. Albumin is described, e.g., in U.S. Pat. Nos. 5,055,407, 5,053,490, 5,051,406, and 5,000,974, the disclosure of each of which is hereby incorporated by reference into this specification.

In one preferred embodiment, the gluten used in this invention contains at least about 89 weight percent of protein, at least 7 weight percent of lipids, and at least 2.0 weight percent of carbohydrates.

Gluten is described in many United States patents. Thus, by way of illustration and not limitation, gluten is described in U.S. Pat. No. 5,030,268 (corn gluten meal), U.S. Pat. No. 5,013,561 (gluten from waxy barley), U.S. Pat No. 5,004,624 (vital wheat gluten), U.S. Pat. No. 4,990,173 (corn gluten meal), U.S. Pat. No. 4,961,937 (high gluten wheat flour), U.S. Pat. No. 4,960,705 (thickened corn gluten), U.S. Pat. No. 4,953,401 (gluten in wheat) U.S. Pat. Nos. 4,950,496, 4,946,699, 4,942,043 (corn gluten meal), U.S. Pat. No. 4,938,976 (wheat gluten of high viscous texture), U.S. Pat. Nos. 4,913,917, 4,911,939, 4,879,133, 4,871,577, 4,861,482, 4,849,239 (PL gluten), U.S. Pat. Nos. 4,826,765, 4,818,557, 4,764,199 (corn gluten meal), and the like. The disclosure of each of these patents is hereby incorporated by reference into this specification As will be apparent to those skilled in the art, many of the gluten materials described above, which may be used in applicants' process, are mixtures of two or more different types of gluten and/or other materials.

In one preferred embodiment, the gluten material used in the process has a particle size distribution, as measured when the gluten is dry (containing less than about 0.1 weight percent of moisture) such that substantially all of the gluten particles are smaller than about 150 microns and, more preferably, are smaller than about 40 microns.

As is well known to those skilled in the art, gluten is a commercially available product which is readily available. Thus, e.g., by way of illustration, one may purchase "vital wheat gluten" from the Zieglers Company of 6890 Kinne Street, East Syracuse, N.Y. as catalog number 058030. Thus, by way of further illustration, one may purchase high gluten flour as either product N4117 or N4146 from the Keck's Meat and Food Service Company of Millerton, Pa.

In the process of this invention, a mixture of gluten and ceramic material is used. It is preferred that at least 10 weight percent of ceramic material (by combined dry weight of gluten [less than 0.1 weight percent of moisture] and ceramic material) be used in the mixture. It is more preferred that at least about 60 weight percent of said mixture of gluten and ceramic material (by dry weight) be comprised of the ceramic material. In an even more preferred embodiment, at least 75 weight percent of ceramic material (by dry weight of ceramic material and gluten) is used in the mixture.

As used in this specification, the term ceramic material refers to a solid material produced from essentially inorganic, non-metallic substances which is preferably formed simultaneously or subsequently matured by the action of heat. See, e.g.. A.S.T.M. C-242-87, "Definitions of Terms Relating to Ceramic Whitewares and Related Products."

By way of illustration, the ceramic material used may be concrete As is known to those skilled in the art, the term concrete refers to a composite material that consists essentially of a binding medium within which are embedded particles or fragments of aggregate.

By way of further illustration, the ceramic material used may be a ceramic whiteware, that is a ceramic body which fires to a white or ivory color. Methods of preparing ceramic whiteware bodies are well known to those skilled in the art and are described, e.g., in U.S. Pat. No. 4,812,428 of Kohut, the description of which is hereby incorporated by reference into this specification.

In another preferred embodiment, the ceramic material is basic brick. As is known to those skilled in the art, basic brick is a refractory brick which is comprised essentially of basic materials such as lime, magnesia, chrome ore, or dead burned magnesite, which reacts chemically with acid refractories, acid slags, or acid fluxes at high temperatures.

In yet another embodiment, the ceramic material is a refractory. As is known to those skilled in the art, a refractory material is an inorganic, nonmetallic material which will withstand high-temperatures; such materials frequently are resistant to abrasion, corrosion, pressure, and rapid changes in temperature. By way of illustration, suitable refractories include alumina, sillimanite, silicon carbide, zirconium silicate, and the like.

By way of further illustration, the ceramic material may be a structural ceramic such as, e.g., silicon nitride, sialon, boron nitride, titanium bromide, etc.

In another embodiment the ceramic material consists essentially of clay or shale. In this embodiment, one preferred shale which may be used is Alfred shale which is commonly available in Alfred, N.Y.

In yet another embodiment, the ceramic material consists or comprises glass. As used in this specification, the term glass refers to an inorganic product of fusion which has cooled to a rigid configuration without crystallizing. See, for example, George W. McLellan et al.'s "Glass Engineering Handbook," Third Edition (McGraw-Hill Book Company, New York, 1984). By way of illustration, some suitable glasses include sodium silicate glass, borosilicate glass, aluminosilicate glass, and the like. Many other suitable glasses will be apparent to those skilled in the art.

The above listing of ceramic materials is merely illustrative, and those skilled in the art will be aware of other suitable ceramic materials such as, e.g., those described in the January, 1991 edition of "Ceramic Industry," Volume 136, No. 1 (Business News Publishing Company, 755 West Big Beaver Road, Suite 1000, Troy, Mich.).

In one preferred embodiment, the composition of this invention is comprised of at least about 70 weight percent of said ceramic material (by weight of ceramic material and gluten, dry basis). In an even more preferred embodiment, the composition of this invention is comprised of at least about 85 weight percent of said ceramic material.

It is preferred that the composition of this invention be comprised of at least 1.0 weight percent of gluten. In one embodiment, one may use at least about 5.0 weight percent of gluten and, more preferably, at least about 10 weight percent of gluten. In another preferred embodiment, the composition is comprised of at least about 20 weight percent of gluten.

In one embodiment, discussed in greater detail elsewhere in this specification, the gluten may be replaced, in part or in whole, by a binder material selected from the group consisting of agar, gelatin, soluble fiber, and mixtures thereof. In this embodiment, the total concentration of the binder material(s) is the same as that specified above for the embodiment where only gluten is used.

In one embodiment, at least about 70 weight percent of the particles of ceramic material are within the range of from about 7 to about 20 microns, and at least about 15 weight percent of the ceramic particles are less than about 7 microns.

The composition of this invention, in addition to containing both gluten and ceramic material, may contain minor amounts (from about 1 to about 10 weight percent) of one or more other materials such as, e.g., pectin, gelatin, cellulose, potatoes and/or other starchy materials, glucose, maltose, eggs, vegetable oil, milk, yeast, sodium bicarbonate or other rising agents), pepsin, and the like. Additionally, or alternatively, one may use enzymes commonly used in baking of breads such as soy flour enzyme, vitamin C, and/or other additives and preservatives commonly used in the baking of bread.

In one embodiment, in which the binder is either a non-gluten material (such as the agar, soluble fiber, or gelatin mentioned above), or a mixture of gluten and non-gluten material, the composition of this invention, in addition to containing such binder material, may also contain minor amounts (from about 1 to about 10 weight percent) of one or more other materials such as, e.g., pectin, gelatin, cellulose, potatoes and/or other starchy materials, glucose, maltose, eggs, vegetable oil, milk, yeast, sodium bicarbonate or other rising agents), pepsin, and the like. Additionally, or alternatively, one may use enzymes commonly used in baking of breads such as soy flour enzyme, vitamin C, and/or other additives and preservatives.

In one preferred embodiment, the ceramic mixture is comprised of from about 1 to about 30 by weight percent (by weight of gluten in the mixture) of a preservative. Suitable preservatives include potassium sorbate, sodium propionate, undecylenic acid, zinc undecylenate, diethylpyrocarbonate, benzoic acid, sodium benzoate, BHA, BHT, sorbic acid, propionic acid, propionates, esters of parahydroxybenzoic acid, and the like. See, e.g., pages 412-413 of John M. DeMan's "Principles of Food Chemistry" (Van Nostrand Reinhold Company, New York, 1980). It is preferred that the preservative be selected from the group consisting of undecylenic acid, sorbic acid, the salt of undecylenic acid, the salt of sorbic acid, and mixtures thereof.

The aforementioned concentrations of gluten, ceramic material, and optional other material(s) are by dry weight bases, total batch. As will be apparent to those skilled in the art, one may determine the concentration of a batch on a dry weight basis by drying the batch until it contains less than about 0.1 weight percent of moisture, and then determining the dry weight percents of each component.

In one embodiment, in addition to containing at least 10 percent (by dry weight) of ceramic material, and the gluten, the composition of this invention also contains from about 5 to about 95 weight percent of water (by total weight of solid material and water). It is preferred that the composition be comprised of from about 25 to about 40 weight percent of water, by total weight of water and solids in the composition.

In one embodiment, the composition contains at least about 60 weight percent of ceramic material, from about 1 to about 40 weight percent of gluten (by combined weight of ceramic material and gluten), and from about 45 to about 75 weight percent of liquid (by combined weight of liquid, ceramic material, and gluten).

In another embodiment, the composition of this invention is comprised of from about 1 to about 30 weight percent of an alcohol of the formula ROH wherein R is alkyl of from about 1 to about 8 carbon atoms. In one aspect of this embodiment, the composition contains both water and alcohol.

FIG. 1 illustrates several preferred processes of applicant's invention. Referring to FIG. 1, it will be seen that, in the process illustrated, the composition is first prepared by a mixing operation 10 prior to the time it is utilized in other process steps.

The gluten or gluten-containing material(s), the ceramic material(s), and any other desired components in applicants, mixture may be mixed by any conventional means. Thus, for example, one may use any of the mixing devices described in J. T. Jones et al.'s "Ceramics: Industrial Processing and Testing" (The Iowa State University Press, Ames, Iowa, 1972). By way of illustration, one may use shell mixers, such as a twin shell or V-mixer, a double cone mixer, and the like. One may use a ribbon mixer. One may use a dry color agitator. One may use a pug mill. Other well-known mixing means will be readily apparent to those skilled in the art.

It is preferred, in one embodiment, to dry mix the ingredients used until a substantially homogeneous mixture is obtained. Thus, e.g., such dry mixing may be done by a ball mill.

After a substantially homogeneous dry mixture of gluten and ceramic material is obtained, water (and/or another liquid) can be added to the mixture to the desired concentration (from 5 to 75 percent, by weight) while mixing is continued. Although other liquids (such as alcohol, polyvinyl alcohol, ethers, ketones, aldehydes, organic solvents, and the like) can be used, it is preferred to use either an aqueous system or water. The water may be added in a pure form, or it may be added while admixed with another material (such as, e.g., in the form of milk).

In many of the applications for applicants' composition, the amount of the water in the composition will vary within the 5%-75% range. Thus, for example, when one desires to use the composition to coat, spray dip, or brush it onto an object, it is preferred that the composition contain from about 45 to about 75 weight percent of water.

In one embodiment, in which corn meal is used as the gluten-containing material, it is preferred to sift the corn meal to remove from it all particles greater than about 100 microns.

Referring to FIG. 1, it will be seen that a mixture from mixing operation 10 may be passed via line 12 to a coating or spraying or dipping or brushing operation 14. In operation 14, a film of the liquid composition is used to coat object to be replicated.

The thickness of the film coated onto the object to be replicated will vary depending upon the intricacy of the detail of the object. Where, for example, one wishes to replicate the shape of a flower, it is preferred to coat a film thickness onto the flower's surfaces which is less than about 0.125 inches (after drying). On the other hand, one often will desire a relatively thick coat, on the order of up to about 6.0 inches.

One may make a mold of an object by coating a relatively thick layer of material onto it and then burning out the object coated. Thus, with regard to the flower, if a relatively thin coat of material is coated onto the flower, and the flower is then burned off, a relatively delicate and fragile replication of the flower will be produced. If, on the other hand, one wishes to produce a mold of the flower (into which one may pour molten metal, e.g.), one should repeatedly coat the flower until the total thickness of the coats is at least several inches so that, when the coated object is fired, a fired body with relatively good physical properties will be produced.

In one embodiment, not shown, after the object to be replicated is initially coated with a relatively thin coat of material (from about 0.1 to about 1.0 inches thick, dry), and such initial thin coat is heat-treated (as described below), a second coat of material is then applied to the object (such as, e.g., by dipping), and the object is heat-treated again. It will be apparent to those skilled in the art that many combinations and sequences of coating/spraying/dipping/brushing together with heat-treating may be utilized.

In general, each time a coat is applied to the object to be replicated by one of the preferred means, such coat should be from about 0.05 to about 0.5 inches. It is preferred to dehydrate the object which has been coated with applicants' composition so that it contains less than about 0.5 weight of moisture. This dehydration may occur in standard dehydrating means (not shown), such as a dessicator. Alternatively, this dehydration may occur in oven 18.

After one or more coats of material have been applied to the object to be replicated, and the coated object has preferably been dehydrated, it is preferred to heat-treat such object in either oven 18 and/or sintering furnace 24.

The coated object may be passed via line 16 to oven 18, wherein it may heated until it has the desired porosity. The porosity may vary from about 5 to about 70 volume percent; it is caused by the evolution of gas from the mixture leaving the mixture during heating. One of the unique factors of applicants' process is that, notwithstanding said gas evolution, the body being heated maintains its structural integrity. Many other ceramic bodies which do not contain gluten will tend to crack upon the evolution of gas (such as water vapor).

In general, when the coated ceramic body is heated in oven 18, it is preferred to heat such object at a temperature of from about 80 to about 450 degrees Fahrenheit for from about 1 minute to about 48 hours until the object contains less than about 0.5 weight percent of moisture. It will be appreciated by those skilled in the art that the higher the temperature used, the shorter the time which will be required.

In one embodiment, illustrated in FIG. 1, the object may be passed directly to the sintering furnace 24 without heating it in the oven; in this embodiment, the dehydration of the coated object occurs in the sintering furnace, preferably as the furnace is raised from ambient to the sintering temperature. Thus, referring again to FIG. 1, the coated object may be passed to oven 18 via line 16 and, thereafter, to sintering furnace 24 via line 22; alternatively, it may be passed directly to sintering furnace 24 via line 20.

The sintering step is generally used when an object with relatively good mechanical properties is required. In general, the coated, dehydrated object is sintered by subjecting it to a temperature of from about 1,500 to about 3,200 degrees Fahrenheit for from about 0.5 to about 24 hours.

In another embodiment of applicants' invention, applicants' composition is charged to a container in which it is allowed to expand and, thus, to conform to the interior shape of the container. In this embodiment, it is preferred to use a composition which contains from about 5 to about 75 percent of water. One may use a dough-like composition (which contains from about 5 to about 30 weight percent of water), one may use a slurry (which contains from about 45 to about 75 weight percent of water), and may use any composition in between.

The composition is charged from mixing operation 10 via line 26 to container 28. It is preferred that container 28 consist of a cavity which describes the shape of an article to be reproduced; and the material will be charged within said cavity and thereafter heat-treated. When it is so heat-treated, it will expand and adopt the shape of said cavity.

Upon sintering, a shaped object will be produced which is substantially identical to the shape of the cavity.

In one embodiment, the container burns off during sintering, leaving only a shaped body which replicates the shape of the cavity. In another embodiment, the container does not burn off during sintering, leaving a container which must be mechanically removed from the shaped object within it.

After the composition has been charged to container 28, it is preferred to dehydrate the composition so that it contains less than about 0.5 weight percent of moisture. One may dehydrate it by passing it to oven 36 via line 32 in the manner described above. Alternatively, one may pass it directly to the sintering furnace 24 where it can be sintered in the manner described above.

Alternatively, one may pass the mixture via line 30 to microwave oven 34. The use of microwave oven 34 dehydrates the coated object relatively rapidly. One may use any conventional microwave, and preferably the coated object will be subjected to microwave radiation at frequency of from about 0.9 to about 22.1 Gigahertz. See, e.g., U.S. Pat. No. 4,872,896, the disclosure of which is hereby incorporated by reference into this specification.

In one preferred embodiment, where microwave oven 34 is used, it is preferred to irradiate the coated object using the "high" setting. In this embodiment, one should preferably subject the coated object to the microwave radiation for at least about 5 minutes per pound of coated object.

One advantage of the microwave oven 34 is that it produces a substantially more homogeneous pore size distribution. Once the coated object has been dehydrated and, when appropriate, heated in the sintering furnace, a porous ceramic structure is produced which has a porosity of from about 1 to 80 volume percent. As will be apparent to those skilled in the art, the porosity of the finished product and the amount of gluten which originally was in the coated material are related.

As is known to those skilled in the art, the porosity of a ceramic object may be determined in accordance with A.S.T.M. Standard Test C373-72 (Reapproved 1982), "Standard Test Method for Water Absorption, Bulk Density, Apparent Porosity, and Apparent Specific Gravity of Fired Whiteware Products."

In one preferred embodiment, the apparent porosity of the center of the finished product is from about 1 to about 15 volume percent. In another embodiment, the apparent porosity of the center of the finished product is from about 16 to about 30 volume percent. In yet another embodiment, the apparent porosity of the center of the finished product is from about 31 to about 45 volume percent. In yet another embodiment, the apparent porosity of the center of the finished product is from 46 to about 80 volume percent.

The center of the finished product of applicants' invention exhibits open cell porosity. Thus, in applicants' structure, there is a predominance of interconnected cells. The test for apparent porosity, mentioned above, determines the effective open cell porosity.

One unique feature of applicants' process is that, even with fired bodies which have in excess of 95 percent of their theoretical density, open (effective porosity still exists). Heretofore, it did not appear to be possible to obtain such a combination of high density and effective porosity. Thus, for example, in the classic work by W. D. Kingery et al. entitled "Introduction to Ceramics," Second Edition (John Wiley and Sons, Inc., New York, 1976), it is disclosed (at page 521) that "Before firing, almost the entire porosity is present as open pores. During firing, the volume fraction porosity decreases . . . Although some open pores are eliminated directly, many are transformed into closed pores. As a result, the volume fraction of closed pores increases initially and only decreases toward the end of the firing process. Open pores are generally eliminated when the porosity has decreased to 5% . . . By the time 95% of theoretical density is reached, the ware is gastight."

The distribution of pores in applicants' finished product is substantially different than the pore distribution obtained in prior art products; and the distribution of pores in applicants' device allows for a more effective flow of liquid and/or gas through the porous structure, providing a combination of optimal surface area and ease of flow properties to the structure. As is known to those skilled in the art, the higher the specific surface area of a filter, the greater the filtration effect. However, when all of the pore sizes in a filter are relatively small, the flow rate of material through the filter may be relatively slow. Applicant's product provides an improved combination of effective filtration and reasonable flow rate properties.

In one preferred embodiment, the center section of one porous product produced in applicants' process by baking contains from about 5 to about 40 volume percent of pores with a mean pore diameter of less than about 1 micron. As is known to those skilled in the art, one may determine the mean pore diameter of the pores of a body by examining the body on a scanning electron microscope. Thus, for example, one may use a DSM 940 Digital Scanning Electron Microscope, which is manufactured by and available from Carl Zeiss Inc., One Zeiss Drive, Thornwood, N.Y.

To determine the mean pore diameter, the object so baked is cut through its centerline using, e.g., a variable speed rotary tool. One may use any suitable variable speed rotary tool such as, e.g., Sears and Roebuck's variable speed rotary tool, model number 9A61003, equipped with a $\frac{1}{8}''$ cone silicon carbide abrasive point (available from Sears and Roebuck Company, Chicago, Ill. 60684).

Once the baked and sintered object has been cut through its centerline, the newly exposed surface is then examined under a camera microscope equipped with a reticle. Thus, e.g., one may use optical microscope, model number SD 3900-00, (available from the Cole-Parmer Instrument Company of 7425 North Oak Park Avenue, Chicago, Ill. 60648) equipped with a Polaroid SX-70 camera (model number SD-3910-00), both of which also are available from the Cole-Parmer Instrument Company. The optical microscope is provided with a reticle, such as reticle 04RET011, available from Melles Griot Company of 1770 Kettering Street, Irvine, Calif. 92714.

Using this equipment, a picture of the ground surface of the sintered ceramic sample is taken, and the number of pores per unit area within a specified pore size range is determined. However, when determining the number of pores which are from about 1.0 micron to 100 microns, it is preferred to use the scanning electron microscope.

In the preferred embodiment described above, it is also preferred that from about 7 to about 60 volume percent of the pores in the center of the finished body, when tested by the aforementioned test, have a mean pore diameter of from about 1 to about 10 microns. As will be apparent to those skilled in the art, reference to the term "about 7 to about 60 volume percent" implies that those pores which have a mean pore diameter of from about 1 to about 10 microns in the center section account for from about 7 to about 60 volume percent of the porosity of the ground section.

In the embodiment described above, and with respect to said section, it is preferred that from about 10 to about 60 volume percent of the pores in the center of the finished body have a mean pore diameter of from about 11 to about 100 microns, that from about 5 to about 65 volume percent of the pores in the center of the finished body have a mean pore diameter of from about 101 to about 500 microns, that from about 3 to about 70 volume percent of the pores in the center of the finished body have a mean pore diameter of from about 501 to about 1,000 microns, and that from about 0 to about 75 volume percent of the pores in the center of the finished body have a mean pore diameter in excess of 1 millimeter.

In one preferred embodiment, wherein the coated body is either baked or microwaved, a "crust" is preferably formed on the outside surface of the object. This crust, which generally is from about 1 millimeter to about 2 centimeters in thickness, has a porosity of from about 1 to about 40 volume percent. In general, the porosity of the crust section is from about 3 to about 40 percent of the porosity of the center section.

As will be readily apparent to those skilled in the art, the pore distribution of the crust can be determined by examining such crust with the equipment and procedures described above. Thereafter, the pore distribution of the center of the sintered body may be similarly examined, and the relationship of the two pore distributions may be determined.

The crust has a pore size distribution, as measured above, such that at least about 15 volume percent of the pores in the finished product have a mean pore diameter of less than 1 micron. As will be apparent to those skilled in the art, this means that those pores in the crust which have a mean pore diameter of less than about 1 micron represent at least 15 volume percent of the total porosity of the crust.

In the embodiment described above, from about 10 to about 60 volume percent of the pores in the crust have a mean pore diameter of from about 1 to about 10 microns, that from about 10 to about 60 volume percent of the pores in the crust have a mean pore diameter of from about 11 to about 100 microns, that from about 1 to about 10 volume percent of the pores in the crust have a mean pore diameter of from about 101 to about 500 microns, that from about 1 to about 7 volume percent of the pores in the crust have a mean pore diameter of from about 501 to about 1,000 microns, and 0 volume percent of the pores in the crust have a mean pore diameter in excess of 1 millimeter.

FIG. 24 is a sectional view which illustrates, for one product 37 which has been baked and sintered in applicants' process, the porosity of the crust section 38 and the center section. It will be seen that the crust section 38 contains smaller pores than center section 40 and, consequently, has a lower porosity.

Referring again to FIG. 1, the composition from mixing operation 10 may be passed via line 42 to molding operation 44. In one preferred embodiment, the composition is molded in operation 44 by hot-pressing. As is known to those skilled in the art, hot pressing is baking during the application of external pressure. In this aspect of the molding process, a pressure of from about 18 to about 175 pounds per square inch and a temperature of from about 200 to about 600 degrees Fahrenheit is used in the hot pressing for from about 1 second to about 10 minutes. It is preferred to hot press the composition at a pressure of about 18 to about 50 pounds per square inch and a temperature of from about 350 to about 450 degrees Fahrenheit for from about 2 to about 5 minutes.

Referring again to FIG. 1, the object which has been molded (such as, e.g., by hot pressing) may be passed directly via line 46 to sintering furnace 24. Alternatively, the object may be passed via line 48 to oven 50, to further dehydrate it until it contains less than about 0.5 weight percent of moisture. One may heat the object in oven 50 to a temperature of from about 100 to about 450 degrees Fahrenheit for a time sufficient to dehydrate it to the desired level.

Thereafter, the dehydrated object may then be passed to the sintering furnace 24 via line 52.

Referring again to FIG. 1, it will be seen that the composition which is subjected to the self-rising operation described elsewhere may be passed directly to sintering furnace 24 via line 56. Alternatively, and as described elsewhere in this specification, the composition may first be charged into microwave oven 34 and thence via line 54 to sintering furnace 24. Alternatively, or additionally, the composition may be charged to oven 36 and thence via line 58 to sintering furnace 24.

Figure 2:
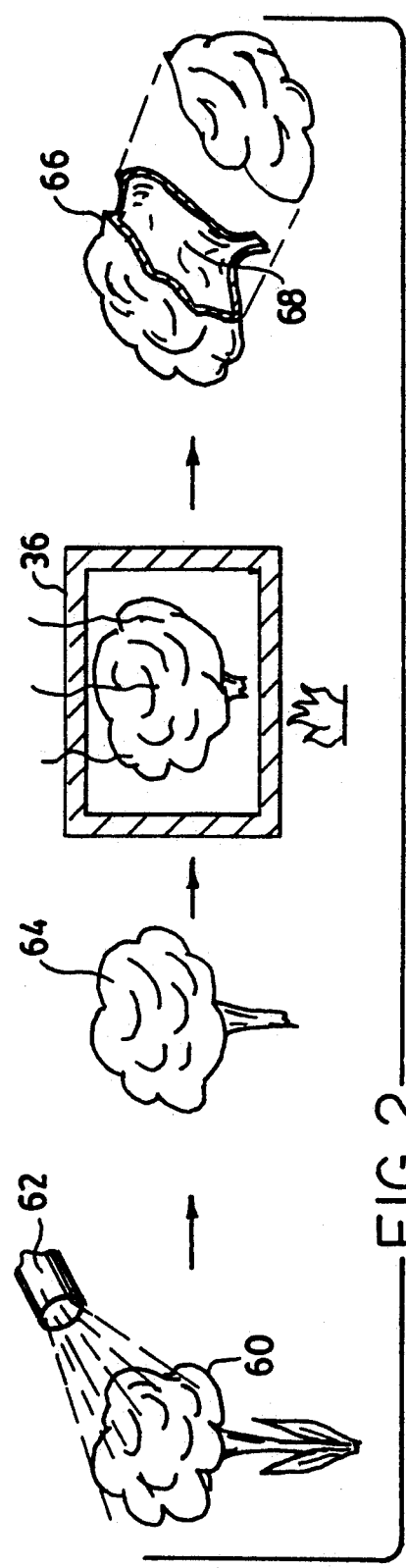
FIG. 2 is a flow diagram illustrating one preferred coating process of the invention.

FIG. 2 illustrates one preferred means of replicating fine objects such as, e.g., a flower 60. Although a flower is used to illustrate this replication process, it will be apparent that any other fine object can be replicated such as, e.g., a poodle.

When replicating fine objects, such as flower 60, it is preferred that the composition used be a water-based slurry which contains from about 40 to about 95 weight percent of water (by combined weight of water and solids). The solid material in the slurry will preferably contain from about 10 to about 40 weight percent of gluten and from about 90 to about 60 weight percent of ceramic material, both by combined weight of gluten and ceramic material.

In one aspect of this embodiment, it is preferred that the slurry used contain the ceramic materials present in casting slips which can produce a porcelain body. These casting slips are well known to those skilled in the art and are described, e.g., in James Chappell's "The Potters Complete Handbook of Clay and Glazes" (Watson-Guptill Publications, New York, N.Y., 1977). Thus, the ceramic portion of the formulation may contain (1) 46 parts of kaolin, 34 parts of flint, 19.8 parts of feldspar, and 1.2 parts of sodium carbonate, (2)22 parts of Kentucky ball clay #4, 20 parts of Tennessee ball clay #1, 58 parts of nepheline syenite, 1.6 parts of sodium carbonate, (3) 51 parts of kaolin, 29.7 parts of feldspar, 19 parts of flint, 0.3 parts of sodium carbonate.

As is well known to those skilled in the art, and as is described in U.S. Pat. No. 4,812,427, the porcelain casting slip often will contain from about 25 to about 39 parts of ball clay, from about 11 to about 25 parts of kaolin, from about 40 to about 55 parts of nonplastics (potassium and sodium aluminosilicates and flint, such as feldspar, nepheline syenite, feldspathic sand, flint, calcined clays, talc, pyrophylite, and the like).

Referring again to FIG. 2, the slurry in sprayer 62 is sprayed onto flower 60 until a coating with a thickness of about 0.06 to about 0.25 inches is produced, thereby producing coated flower 64. In one embodiment, the coated flower 64 is then charged to oven 36, where it is preferably heated under atmospheric conditions to a temperature of from about 100 to about 450 degrees Fahrenheit until it contains less than about 0.5 weight percent of moisture; the amount of moisture in the coated flower 64 may be determined by conventional means. In another embodiment, not shown, the coated flower 64 may be charged directly to sintering furnace 24, in which, as the temperature is slowly raised, it becomes dehydrated and sintered. In this latter embodiment, it is preferred to raise the temperature of the furnace at a rate of from about 1 to about 5 degrees Fahrenheit per minute.

Once flower 64 has been suitably dehydrated in oven 36, it may be either coated and dehydrated again, and/or charged to a sintering furnace 24 (not shown).

When the coated flower 64 is in the sintering furnace 24, it usually will be subjected to a temperature of from about 1,100 to about 2,600 degrees Fahrenheit and, thus, will have its organic portion burned out. Thus, the flower 60 and the gluten in the composition will burn out, leaving a porous, sintered replica 66 of the flower 60 with a hollow, replicated core 68.

Figure 3:
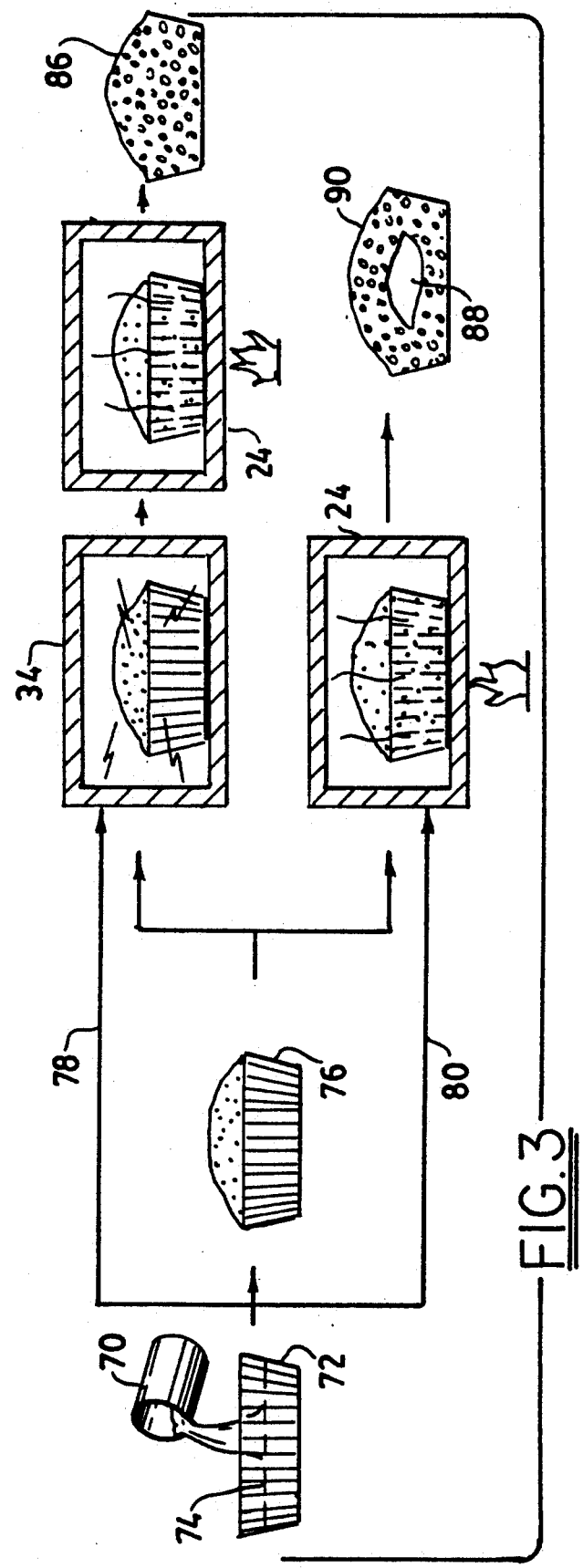
FIG. 3 is a flow diagram illustrating one preferred baking process of the invention.

FIG. 3 illustrates a baking process in which the composition of this invention expands during baking to fill a cavity within a mold. Referring to FIG. 3, it will be seen that container 70 is comprised of applicants' composition which, preferably, contains from about 20 to 60 weight percent of water (by total weight of composition). This composition is charged into mold 72 until it fills a portion of such mold. Because the water/- ceramic/gluten mixture expands during baking, it is preferred to fill mold 72 only up to about line 74 so that the mold 72 is only partially filled. In general, from about 20 to about 60 volume percent of the mold is filled with the composition, although it is preferred to fill mold 72 so that about 45 to about 55 volume percent of it is filled.

In one embodiment, yeast and/or one or more enzyme(s) are added to the composition, causing it to rise without heating and produce the risen loaf 76. In another embodiment, the partially filled mold 72 is passed via line 78 and/or 80 for further thermal processing.

Referring again to FIG. 3, either the partially filled mold 72 and/or the risen loaf 76 can be treated in microwave oven 34 and thereafter treated in sintering furnace 24 to produce porous sintered body 86. In this embodiment, the material is first baked in the sintering oven (at a temperature of from about 100 to about 450 degrees Fahrenheit) and thereafter sintered. It should be noted that, inasmuch as the mold 72 consisted of organic material in the embodiment illustrated in FIG. 3, it burned out during sintering, leaving only the porous ceramic body 86.

Referring again to FIG. 3, either the half-filled mold 72 and/or the risen loaf 76 may be charged directly to sintering furnace 24, in which it may also be initially baked and thereafter sintered. In some situations, which are illustrated in FIG. 3, the direct baking and subsequent sintering of the risen loaf sometimes will cause a cavity 88 to for in sintered body 90. This phenomenon generally does not occur when the composition is first subjected to microwave treatment.

FIG. 4 illustrates a relatively low-temperature low-pressure molding process. In this embodiment, the composition of this invention is charged to a container 92. This composition may contain from about 20 to about 60 weight percent of water. The composition from container 92 may be charged onto the forming surfaces of hot waffle iron 94, usually to a thickness of from about 0.25 to about 1.0 inch. Thereafter, the waffle iron 94 is closed, subjecting the aqueous composition to a slight pressure. The composition is maintained within waffle iron 94 for from about 1 to about 10 minutes, thereby forming waffle 96. The temperature within waffle iron 94 is generally from about 200 to about 450 degrees Fahrenheit.

The waffle 96 is then charged to sintering furnace 24 where it is subjected to a temperature of from about 1,100 to about 2,600 degrees Fahrenheit to form a sintered body 98.

FIGS. 5, 6, 7, and 8 illustrate one preferred use of applicants' process to make a ceramic burner element which, when used with a liquid fuel, acts as a ceramic wick. Referring to these Figures, it will be seen that ceramic wick 100 ring to these Figures, it will be seen that ceramic wick 100 is preferably comprised of contiguous layers 102 and 104, each with different porosities. The wick 100 is disposed within a pool of flammable liquid 106 (such as kerosene), or natural gas 106 (such as propane), and the upward flow of said liquid or gas is partially prevented by the presence of barrier 108. Because the porosity of layer 102 is lower than that of layer 104, the liquid fuel 106 is wicked up layer 102 and may be ignited to form flame 110.

Figure 8:
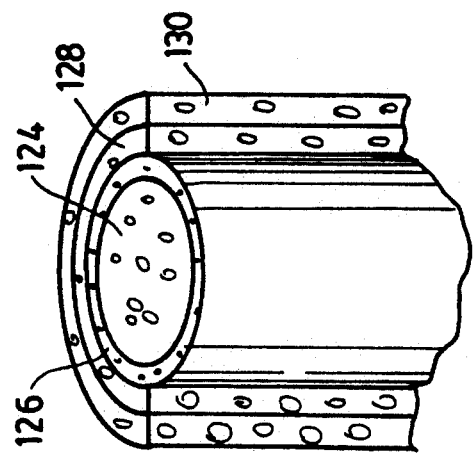

As will be apparent to those skilled in the art, the ceramic wick 100 may be comprised of many layers with many different arrangements of porosity, thickness, and configuration. Thus, by way of illustration, and referring to FIG. 6, the wick of this embodiment has an inner layer 112 with a larger porosity than that of intermediate layer 114 or outer layer 116. Thus, by way of further illustration, the wick of FIG. 7 is comprised of an outer layer 118, an inner layer 120, and a reflector 122 which tends to direct the heat produced by the wick. Thus, by way of further illustration, the ceramic wick of FIG. 8 is comprised of an inner layer 124 with a relatively large porosity, a first intermediate layer 126 with a smaller porosity, a second intermediate layer 128 with a porosity larger than that of the inner layer 124, and an outer layer 130 with a porosity larger than that of the inner layer 124. As will be apparent to those skilled in the art, by sequentially coating and firing an object with different gluten/ceramic compositions, one may form contiguous layers of material with different porosities.

Figure 9:
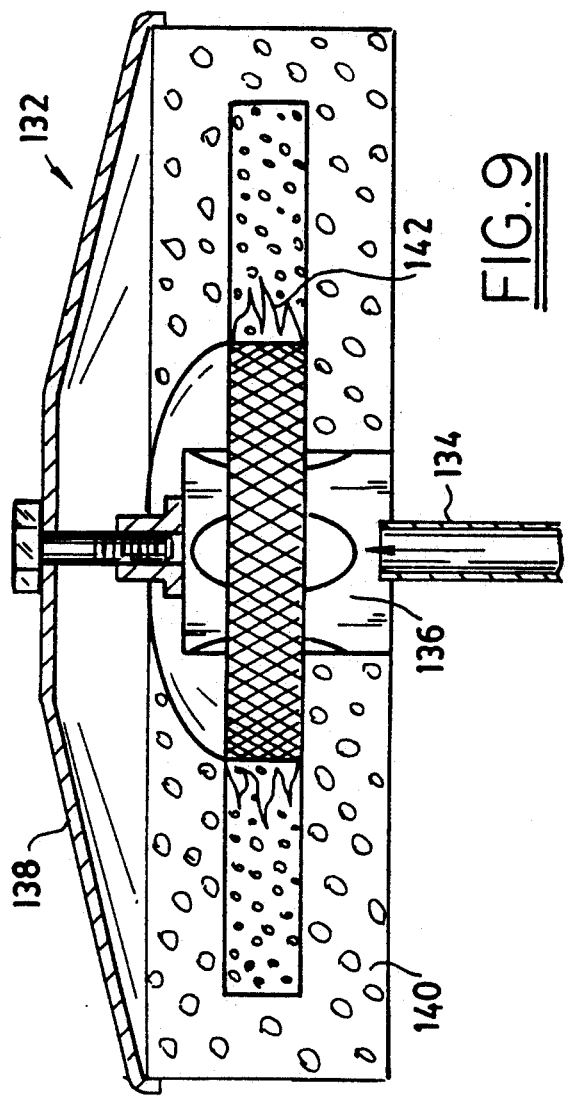
FIG. 9 illustrates a burner assembly which may be produced by the process of this invention.

FIG. 9 illustrates a burner assembly 132 which is comprised of a gas inlet 134, valve 136, cap 138, and ceramic diffuser body 140. Depending upon the pressure of the gas fed into the diffuser, a flame 142 can be caused to appear at various points of the ceramic body 140.

Figure 10:
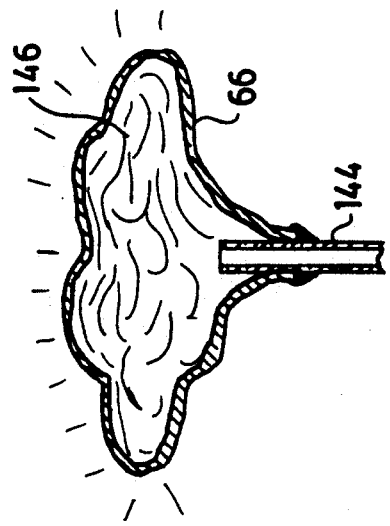
FIG. 10 illustrates a particular ceramic body made from the composition of this invention.

FIG. 10 illustrate the sintered body 66 connected to a source of neon plasma (not shown) by pipe 144. Disposed within pipe 144 is an electrode (not shown) which will excite the plasma 146.

Figure 11:
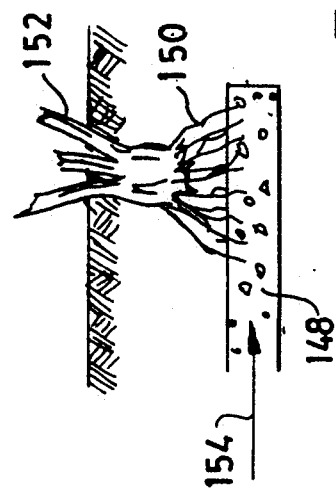
FIG. 11 illustrates the use of plant growing media made from one of the preferred compositions of this invention.

FIG. 11 illustrates the use of a porous body 148 to feed nutrients to the roots 150 a plant 152 and to act as an anchoring medium. Both water and nutrients may be fed in the direction of arrow 154 into body 148, to which roots 150 are attached and with which they communicate.

Figure 12:
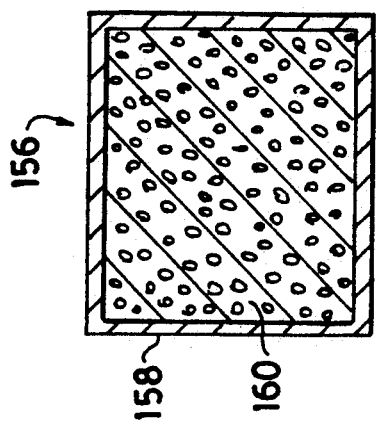
FIG. 12 illustrates a filter made from one of the compositions of the invention.

FIG. 12 is a sectional view illustrating a particulate filter 156. Filter 156 is comprised of frame 158 and filter body 160.

Figure 13:
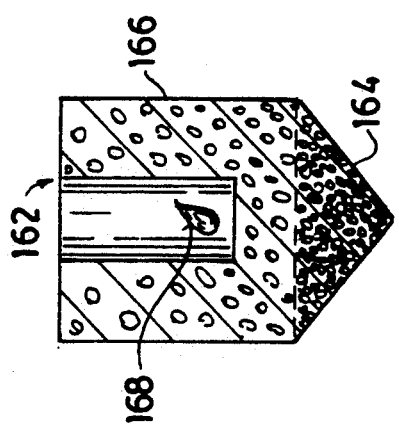
FIG. 13 is a sectional view of a seed capsule made from one of the compositions of the invention.

FIG. 13 is a sectional view illustrating a planting pellet 162 which is comprised of wedge 164, porous ceramic container 166, and seed 168. The entire pellet is inserted into the ground. As the seed germinates, its roots spread through ceramic container 166.

In one embodiment, the porous ceramic container 166 is comprised of or consists essentially of a ceramic material which is partially water soluble and will release nutrients gradually. These water-soluble glasses are well known to those skilled in the art.

Figure 14:
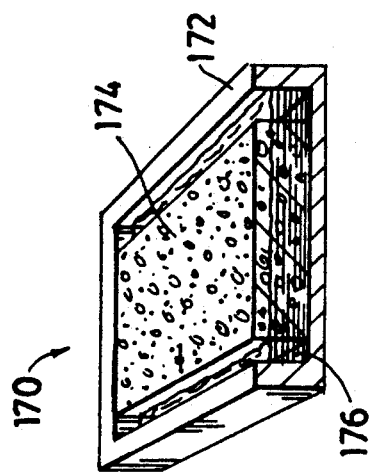
FIGS. 14, 15, and 16 illustrate the use of the composition of the invention as a plant growing medium.

FIG. 14 illustrates a hydroponic container 170 which is comprised of wall 172, porous medium 174, and liquid 176. Plants may extend roots through the pores of medium 174 towards liquid 176. As will be apparent to those skilled in the art, the liquid 176 may be a suitable nutrient solution.

Figure 15:
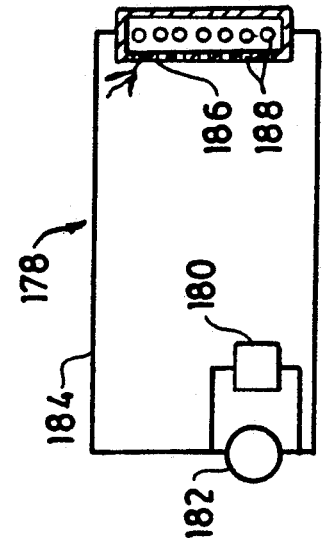

FIG. 15 illustrate yet another hydroponic system 178 which is comprised of a reservoir 180 of nutrient solution which is connected to a pump 182. Pump 182 forces nutrient solution through pipe 184 into the top of pipe 186. Within pipe 186 is disposed a porous ceramic body (not shown). Holes 188 in pipe 186 allow the roots of plants (not shown) to communicate with the porous ceramic body within pipe 186.

Figure 16:
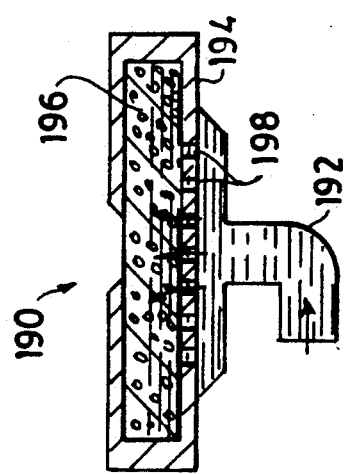

FIG. 16 is a sectional view of a hydroponic apparatus 190 comprised of a nutrient fluid input 192, a holder 194, a porous ceramic body 196 disposed within and retained by holder 194, and aeration vents holes 198. In the operation of this device 190, nutrient fluid is forced up through said delivery pipe 192 and aeration vent holes 198 and communicate with a plant (not shown) contiguous with the surface of ceramic body 196.

Figure 17:
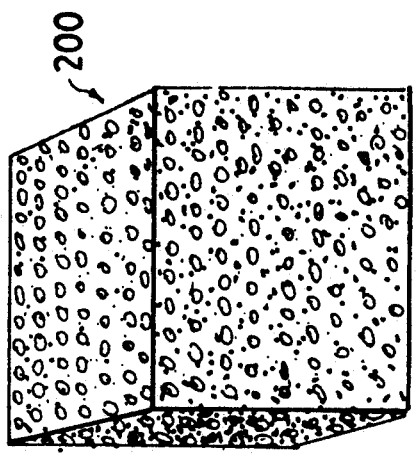
FIG. 17 illustrates a porous ceramic material made by a preferred process of the invention which may be infiltrated by polymeric material.

FIG. 17 illustrates a means of forming a composite material. In accordance with the process described elsewhere in this specification, a porous, sintered ceramic body 200 is formed. Thereafter, by conventional infiltration techniques, either molten polymeric material (such as, e.g., synthetic polymers such as nylon, polyester, Kevlar, polyvinyl chloride, and the like) and/or molten metal is infiltrated partially or completely into the surface(s) of the porous body 200.

Figure 18:
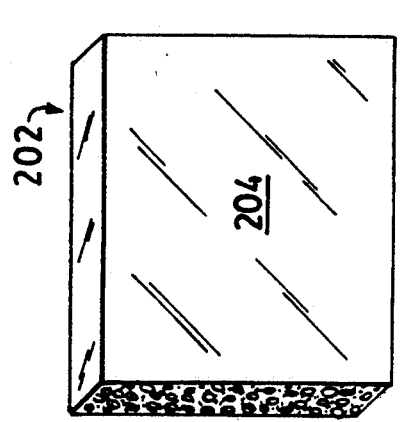
FIG. 18 illustrates a porous tile made by one preferred process of the invention.

FIG. 18 is a perspective view of a roof tile 202 made by the process of this invention. In the embodiment illustrated, the exterior surfaces 204 of roof tile 202 are glazed.

PREPARATION OF A CERMET BY ELECTROCHEMICAL MEANS

In one preferred embodiment of this invention, a cermet material is provided by an electrochemical process in which one of the electrodes is disposed within a porous body which, preferably, is made by the process of this invention. This process is illustrated in FIG. 19.

Figure 19:
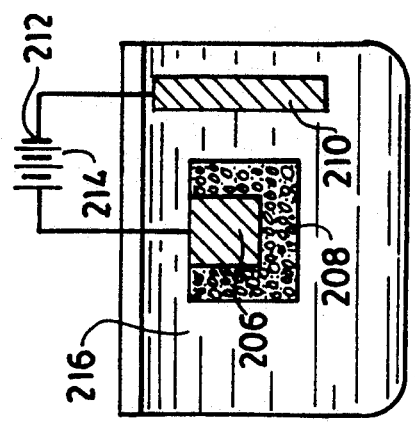
FIG. 19 illustrates a cermet material made by one preferred process of the invention.

Referring to FIG. 19, a metal cathode 206 is disposed within a porous ceramic body 208 which has open cell porosity. Porous ceramic body 208 may be made by the process of this invention, or it may be made by other processes, as long as it has open cell porosity.

In one embodiment, ceramic body 208 is made by the process of this invention by coating applicants' ceramic composition onto a metal substrate and then firing the coated metal substrate. In another preferred embodiment, the ceramic porous body 208 is first prepared, and cavity is provided within it, and the metal cathode is disposed within it.

Referring again to FIG. 19, metal anode 210 is connected to the negative terminal 212 of power source 214. Electrons flow from power source 214, to anode 210 (where metal ions are formed), through solution 216, to cathode 206. As will be apparent to those skilled in the art, solution 216 preferably is comprised of a solution of a metal compound wherein the metal cation is the metal of anode 210. The metal ions in solution 216 pass through the pores of porous body 208 and accrete upon the surface of metal cathode 206. As this process continues, the pores of the ceramic body 208 become filled with metal.

In one preferred aspect of this embodiment, after the electroplating operations has been completed, the metal cathode/ceramic body assembly is then placed in an oven (not shown) and heated to more firmly and homogeneously distribute the metal throughout the pores of ceramic body 206.

Figure 20:
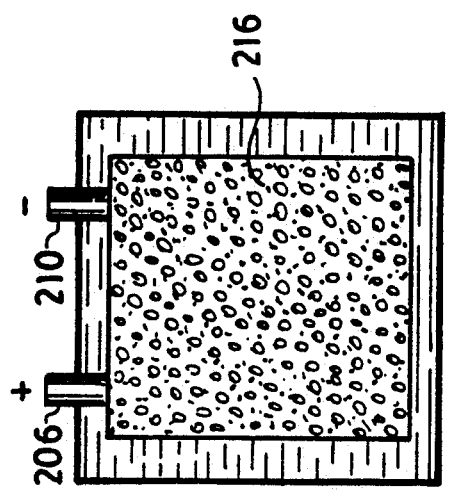
FIG. 20 illustrates a battery made by one preferred process of the invention.

As will be apparent to those skilled in the art, when the metal of anode 210 differs from the metal of cathode 206, a potential difference arises. Thus, if one removes the power source from the device of FIG. 19, a battery results. This battery structure is illustrated in FIG. 20.

Figure 21:
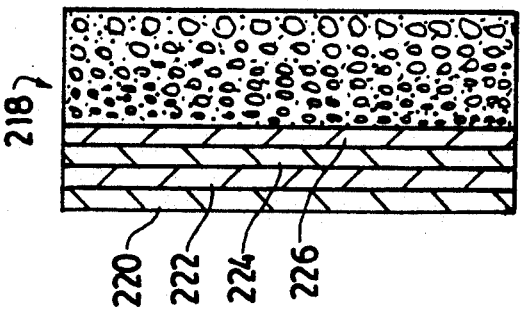
FIG. 21 illustrates a bone patch material made by a preferred process of the invention.

FIG. 21 illustrates a bone patch material which can be made by the process of this invention. Referring to FIG. 21, bone patch is preferably comprised of a multiplicity of layers such as laminated layers 220, 222, 224, 226. These laminar layers may be made by the sequential deposition process described elsewhere in this specification. They resemble the laminar structure of many bones and, thus, should be compatible therewith. In one aspect of this embodiment, the ceramic material used is calcium phosphate.

Because of the flexibility of applicant's process, one can produce a bone-like structure with a porosity distribution which closely simulates that of naturally-occurring bone.

Figure 22:
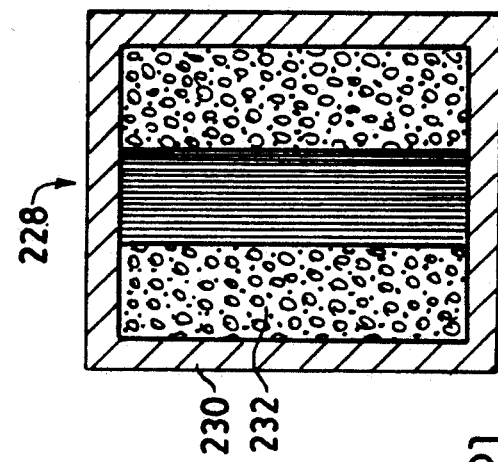
FIG. 22 illustrates a waste disposal core made by a preferred process of the invention.

FIG. 22 illustrates a toxic waste disposal container 228 which is comprised of an impervious outer shell 230, a porous intermediate layer 232. If, by some accident, container 228 were to rupture, porous material 232 would tend to absorb and retain the toxic waste.

Figure 23:
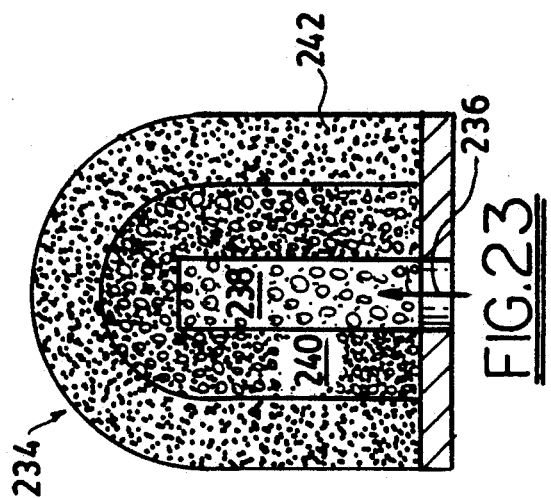
FIG. 23 is a sectional view of a burner core which may be made by the process of this invention.

FIG. 23 illustrates a burner core 234 into which pressurized gas is fed in the direction of arrow 236. By varying the porosities of layers 238, 240, and 242, one can affect the occurrence and intensity of the flame within this core.

FIG. 25 illustrates a forming process in which a ceramic green body is first formed around one or more noodles 240 which are comprised of gluten-containing material. These noodles may be formed by conventional noodle-forming techniques to any desired shape(s). Thereafter, either a ceramic material (such as clay) or a ceramic/gluten mixture (such as applicant's composition) is formed around them. The green body is then processed so that, ultimately, the noodles and/or the gluten burn out. A sintered ceramic body 250 comprised of channels where the noodles 248 had appeared and pores (in case a ceramic/gluten mixture is used) are formed.

FIG. 26 illustrates a process in which a metal casting body may be formed. Referring to FIG. 26, it will be seen that, in the first step of this process, the object to be replicated 252 (a tree branch) is coated with the composition of the invention to form a coated body 254 which, thereafter, is fired to form a hollow sintered body 256. Molten metal 258 is poured within the cavity of body 256 and allowed to cool. Thereafter, the ceramic shell of body 256 is broken off the cooled metal by conventional means such as, e.g., hammer 260, and the metal replica 262 of the object to be replicated 252 is removed.

Preparation of a Filter Body with Substantial Porosity

Figure 27:
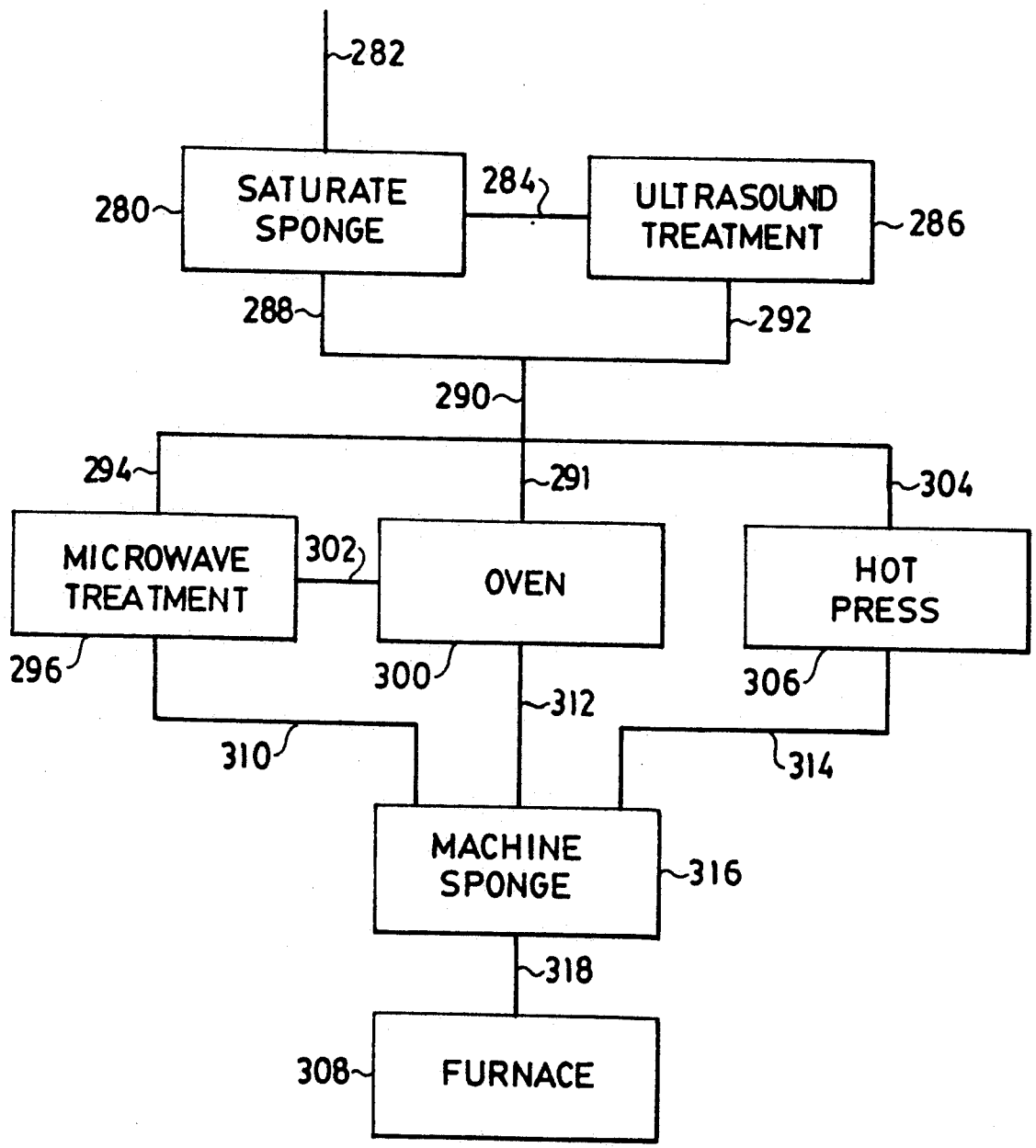
FIG. 27 is a flow diagram of a process for producing a filter body with a substantial effective porosity.

FIG. 27 is a flow diagram illustrating a preferred process of applicants' invention in which a body with substantial porosity and pore distribution uniformity is produced.

The distribution of pores in applicants' finished product is substantially different than the pore distribution obtained in prior art products; and the distribution of pores in applicants' device allows for a more effective flow of liquid and/or gas through the porous structure, providing a combination of optimal surface area and ease of flow properties to the structure.

The properties of the porous body made in accordance with the procedure of FIG. 27 are similar to the properties of the porous bodies described elsewhere in this specification. However, one substantial difference is that less than 1.0 volume of the pores in the body produced by the process of FIG. 27 are larger than the maximum pore size of the sponge-like material used in such process. Thus, depending upon the properties of the sponge-like material chosen for the process, the pore size distribution also will vary.

In one embodiment, the average pore diameter of the sponge used in applicants' process does not exceed 3.0 centimeters. In another embodiment, the average pore diameter of the sponge-like material used in applicants' process does not exceed 1.0 centimeter. In yet another embodiment, the average pore diameter of the sponge-like material does not exceed 500 microns. In yet another embodiment, the average pore diameter of the sponge-like material does not exceed 100 microns. In yet another embodiment, the average pore diameter of the sponge-like material does not exceed 20 microns.

Referring to FIG. 27, and in the preferred process described therein, a sponge-like material (not shown) is saturated in step 280.

As is known to those skilled in the art, a sponge is an material is an organic (carbon-containing) material which be any of numerous, primitive, chiefly marine animals of the phylum Porifera composed of fibrous material. Furthermore, any of various substances having spongelike qualities (such as certain forms of plastics, rubber, or cellulose) also may be used as sponge in applicants' invention.

Thus, by way of illustration and not limitation, the sponge material used in the process may be the cellular skeleton of a marine animal of the genus Spongia.

Thus, by way of further illustration, the sponge material may be a cellular plastic. As is known to those skilled in the art, a cellular plastic is a thermosetting or thermoplastic foam composed of cellular cores with integral skins having high strength and stiffness; the cells result from the action of a blowing agent, either at room temperature or during heat treatment of the plastic material.

By way of further illustration, the sponge material may be a solid foam (such as sponge rubber), which is a disper the action of a blowing agent, either at room temperature or during heat treatment of the plastic material.

By way of further illustration, the sponge material may be a solid foam (such as sponge rubber), which is a dispersion of gas in a liquid or solid.

By way of further illustration, one may use the organic sponge-like materials described in U.S. Pat. No. 5,035,468 (open cell organic sponge), U.S. Pat. Nos. 5,107,861, 5,106,969 (marine sponge), U.S. Pat. No. 5,105,827 (elastic foam sponge), U.S. Pat. Nos. 5,104,350, 5,103,729, 5,100,384, 5,099,684, 5,099,541, 5,096,946 (cellulosic sponge), 5,093,381 (rubber sponge), U.S. Pat. No. 5,091,412 (marine sponge), U.S. Pat. No. 5,081,740 (sponge rubber), U.S. Pat. Nos. 5,073,202, 5,071,648 (polyvinyl acetate sponge), U.S. Pat. No. 5,071,347 (synthetic sponge), U.S. Pat. No. 5,058,211 (polyurethane sponge), U.S. Pat. Nos. 5,039,414, 5,018,300, 5,013,660 (sponge plastic), U.S. Pat. No. 4,991,841 (sponge rubber), U.S. Pat. No. 4,959,341 (polyanionic carbohydrate), U.S. Pat. No. 4,957,810 (synthetic sponge), U.S. Pat. No. 4,925,924 (collagen sponge), U.S. Pat. No. 4,925,327 (foam sponge), U.S. Pat. No. 4,904,469 (polysaccharide sponge), and the like. The entire disclosure of each of these United States patents is hereby incorporated by reference into this specification.

The sponge material used in the process of this invention is preferably organic. The term organic, as used in this case, refers to a sponge material which, when subjected to a temperature of 800 degrees Celsius for 60 minutes, will "burn out," i.e., will be substantially entirely converted to gaseous material. As those skilled in the art are aware, the sponge material may contain some impurities which will not vaporize at 800 degrees Celsius. However, as long as at least about 95 weight percent of the sponge material is converted to gas when subjected to 800 degrees Celsius for 60 minutes, such material may be used in applicants' process.

In one preferred embodiment, the sponge-like material used in applicants' process is either an elastic foam sponge (sold under the name of "O-CELL-O" by the Minnesota Mining and Manufacturing Corporation), a polyurethane foam sponge. In another embodiment, the sponge material is loofa.

The ceramic mixture described elsewhere in this specification is preferably in the form of a slurry, and such slurry preferably is used to substantially saturate the sponge material. In this embodiment, the slurry contains from about 45 to about 75 weight percent of solid material and from about 55 to about 25 weight percent of liquid, such as water. Referring to FIG. 27, the slurry (not shown) may be charged via line 282.

The ceramic mixture which is described elsewhere in this specification, which is preferably comprised of ceramic material and gluten, is used to substantially saturate the sponge material so that said sponge material contains from about 95 to about 100 percent of the maximum amount it can hold of such mixture. One can determine the maximum amount of slurry that can be held by determining the weight of slurry in a container, thereafter compressing the sponge material until it has attained its state of substantial maximum density, thereafter immersing the compressed sponge material in the slurry, and thereafter removing the compressive force upon the sponge material and allowing it to expand and pick up slurry, and thereafter removing the sponge material from the slurry. The container with the slurry can then again be weighed to determine the amount of slurry picked up. This is the saturation amount.

The sponge saturation process may be conducted under ambient conditions. Alternatively, one may use super- or subatmospheric pressure conditions.

Any conventional means may be used to substantially saturate the sponge material. Thus, e.g., the sponge material may be immersed in the slurry, the slurry may be sprayed onto and/or through the sponge material, etc.

When the sponge material used in the process of FIG. 27 has a maximum pore size of less than about 600 microns, it is preferred to subject the substantially saturated sponge material to ultrasound treatment. Thus, referring to FIG. 27, the saturated sponge may be passed via line 284 to ultrasound chamber 286 and exposed to ultrasonic vibration at a frequency of greater than about 20,000 hertz for at least about 5 minutes.

After the sponge material has been saturated and, optionally, subjected to ultrasonic treatment, it is dehydrated until it contains less than about 5.0 weight percent of liquid. It is preferred to conduct the dehydration until the sponge material contains less than about 2.0 weight percent of liquid. It is even more preferred to dehydrate the sponge material until it contains less than about 1.0 weight percent of liquid. In the most preferred embodiment, the sponge material is dehydrated until it contains less than about 0.5 weight percent of liquid.

Any conventional means may be used to dehydrate the saturated sponge material. Thus, for example, one may allow to air dry, heat it under vacuum or under ambient conditions, flow air (or other gas) over the sponge material, charge the sponge to a dessicator, etc.

Three preferred dehydrating means are illustrated in FIG. 27. Thus, referring to FIG. 27, the saturated sponge which has not been subjected to ultrasonic frequency may be charged via line to line 290. The saturated sponge which has been subjected to ultrasound treatment may be charged via line 292 to line 290.

Referring again to FIG. 27, in one embodiment, the saturated sponge is passed via lines 290 and 294 to microwave chamber 296. In general, for each 50 grams of weight of saturated sponge, the sponge will be subjected to microwave radiation for at least about 40 seconds and, preferably, for at least 60 seconds. It is preferred not to expose the saturated sponge for more than about 2 minutes for each 50 grams of saturated sponge.

Alternatively, one may pass the saturated sponge via lines 290 and 298 to oven 300. Additionally, the microwaved sponge from microwave unit 296 may also be passed via line 302 to oven 300.

It is preferred to heat the saturated sponge in oven 300 to a temperature of from about 300 to about 450 degrees Fahrenheit and subject the sponge to such temperature for at least about 2 minutes. In one embodiment, the saturated sponge is heated for from about 10 to about 30 minutes at a temperature of from about 325 to about 375 degrees Fahrenheit.

In another embodiment, the saturated sponge is passed via lines 290 to hot press 306. The hot pressing conditions described previously in this specification may be used in hot press 306 to dehydrate and/or form the sponge material. Thus, e.g., one may use a waffle-iron type of apparatus to dehydrate and form the saturated sponge.

In one embodiment, during the microwave treatment and/or the oven heating treatment and/or the hot pressing treatment, the saturated sponge material may be enclosed within a mold so that, while it is being dehydrated, it will tend to take the shape of the mold.

In one embodiment, illustrated in FIG. 27, the dehydrated sponge material may be machined prior to the time it is fired in furnace 308; thus, the dehydrated sponge may be passed via line 310, or 312, or 314 to machining operation 316. This machining step, which is optional, may be used to grind one or more of the sponge's surfaces, to cut the sponge to a desired shape, to drill holes in the sponge material, and the like. Applicants' process produces a dehydrated sponge with sufficient green strength to allow such machining operations.

The dehydrated sponge, with or without machining, is passed via line 318 to furnace 308, where it is heated to a temperature of at least about 1,500 degrees Fahrenheit and, preferably, from about 1,500 to about 3,200 degrees Fahrenheit in accordance with the procedure described elsewhere in this specification. During this firing process, the sponge material burns out, leaving a fired, strong, porous ceramic body. This ceramic body may be treated and/or used as described elsewhere in this specification.

In one preferred embodiment, not shown, the gluten is mixed with a glaze composition. In this embodiment, from about 1 to about 15 weight percent of gluten is mixed with from about 99 to about 85 weight percent of glaze. The incorporation of the gluten into the glaze composition will flocculate the glaze and prevent it from flaking, cracking, crawling, creeping, and pinholing.

The following examples are presented to illustrate the claimed invention but are not to be deemed limitative thereof. Unless otherwise specified, all temperature are in degrees Celsius, and all parts are by weight.

EXAMPLE 1: REPLICATION OF THE SHAPE OF A FLOWER

In the experiment of this Example, a daffodil which was obtained at the Alfred Greenhouse of in Alfred, N.Y. was coated with a specified mixture and then burned out. This daffodil was approximately 4 inches in length after the stem was cut.

The mixture used to coat the daffodil contained kaolin, silica, feldspar, soda ash, and gluten. This mixture was prepared by charging 46 grams parts of "EPK kaolin," 34 grams of flint, 19.8 grams of feldspar, and 1.2 grams of soda ash to a 1-gallon bucket; each of these ingredients, as it was charged to the bucket, was sifted through a 100 mesh sieve.

The ingredients were mixed for about 15 minutes until a substantially homogeneous mixture was obtained. Thereafter, to this mixture was charged 25 grams of vital wheat gluten which was purchased from the Zieglers Company of 6890 Kinne Street, East Syracuse, N.Y. as catalog number 058030. This mixture also was sifted and hand mixed for about 15 minutes.

To this mixture was charged 100 grams of water to produce a 80 weight percent slurry. The water/solids mixture was then charged to a blender.

The slurry in the blender was blended at a medium speed for 15 minutes. Thereafter, blended slurry was charged to a spray gun.

The surfaces of the daffodil were then sprayed with the material in the spray gun until each of the surfaces was coated with material with a thickness of about 0.0625 inches. The coated daffodil was then dried by placing it into a test kiln. The temperature of the kiln was 93 degree Celsius, and the coated flower was maintained at this temperature for 10 minutes.

The dried flower was then removed from the kiln, and another coat of material of about 0.0625 inches was sprayed onto it. Thereafter, the flower was then put back into the kiln and fired to cone 9.

The fired object, which replicated the shape of the daffodil, was then removed from the kiln.

EXAMPLE 2: REPLICATION OF THE SHAPE OF A CARNATION

The procedure in example one was used to coat a carnation. The ceramic gluten mixture was prepared in the same manner as in example 1. The carnation was spray coated and charged to a 93 degree Celsius kiln for 15 minutes, removed and sprayed a second time, and placed in the 93 degree kiln for an additional 40 minutes. The coated carnation was then removed from the kiln and dipped in a second mixture that was prepared with the same materials and proportions as in example one with the exception of the water content. The water content was reduced to 50.4 grams of water to produce a 40 weight percent slurry. After dipping the coated carnation in the 40 weight percent slurry, a 0.25 inch coat of material was obtained around the carnation. The carnation was then charged to a microwave oven. The coated carnation was then microwaved on the HI setting for 4 minutes. After microwaving, the carnation was dipped in the 40 weight percent slurry, producing a second 0.25 inch coating, and microwaved for an additional 6 minutes. The carnation was then charged to a test kiln and fired to cone 9. The fired object of this example had a hollow interior, where the carnation had been burned out.

EXAMPLE 3: REPLICATION OF THE SHAPE OF A FLOWER

The procedure of Example 1 was repeated, with the exceptions a daisy was used instead of a daffodil and the kiln drying procedure of the coated daisy required some additional steps. The daisy was prepared in the following manner. The stem of the daisy was cut off close to the head of the flower and placed face down on a block of wood and the back surface of the daisy was spray coated to a thickness of 0.0625 inches. The block of wood with the daisy on it was charged to a 93 degree Celsius kiln for 10 minutes and removed. The daisy was the turned over and spray coated to a thickness of 0.0625 and placed into the kiln for 10 minutes. This procedure was repeated until a coating thickness of 0.125 inches was built up on both front and back surfaces of the daisy. The coated daisy was charged to a kiln and fired in the same manner as in example 1. After the replicated object was removed from the kiln, it was coated with a clear glaze. Thereafter, the coated object was fired at cone 9.

EXAMPLE 4: REPLICATION OF THE SHAPE OF A BURDOCK BUSH

The procedure of Example 1 was repeated, with the exception that a burdock bush was used instead of a daffodil. Before spraying occurred the burdock bush was cut into 6 inch lengths just below a break on the stem of the bushes. The 6 inch cut stems were tied together at the bases with a piece of string. The surface coating and kiln firing procedure of example 1 was then used to finish the piece. After the replicated burdock branches were removed from the kiln they were coated with a clear glaze. Thereafter, the burdock was then put into a test kiln and fired to cone 9.

EXAMPLE 5: REPLICATION OF THE SHAPE OF A FLOWER

In the experiment of this Example, a rose which was obtained at the Alfred Greenhouse was coated with a specified mixture and then burned out. This rose was approximately 2 inches in length after the stem was cut.

The mixture used to coat the rose was substantially identical to the mixture used in Example 1.

The surfaces of the rose were then sprayed with the material in the spray gun until each of the surfaces was coated with material with a thickness of about 0.0625 inches. The coated rose was then dried by placing it into a kiln. The temperature of the kiln was 93 degrees Celsius, and the coated flower was maintained at this temperature for 10 minutes.

The dried flower was then removed from the kiln, and another coat of material of about 0.0625 inches was sprayed onto it. Thereafter, the flower was then put back into the kiln, and the temperature of the kiln was increased from 93 degrees Celsius to cone 9.

After cooling, the fired object, which replicated the shape of the rose, was then removed from the kiln.

EXAMPLE 6: HEAT TREATED CERMET ELECTROPLATE

The ceramic gluten batch mixing procedure of example 1 was followed for this example. In this example a 1 inch by 4 inch piece of galvanized window screen obtained from Binghamton Hardware Co. Inc. 101 Eldredge Street Box 927 Binghamton N.Y. 13902. was dipped in the ceramic gluten mixture. A coating of 0.25 inches thickness was obtained on the surfaces of the sheet metal. The coated piece of metal was charged to a test kiln and fired to a temperature of 950 degrees Celsius over a period of 3 hours. After reaching a temperature of 950 degrees Celsius, the kiln was turned off and allowed to cool to ambient. The coated screen was then removed from the kiln and placed into a salt bath mixture containing 80 grams copper sulfate (obtained from the Fisher Scientific Chemical Manufacturing Division, Fairlawn N.J. 07410 catalog number C-490) which was diluted in 1000 grams of water. The anode of a battery charger was connected to a piece of copper. The cathode of the battery charger was then connected to the piece of coated metal. Both the copper and the coated metal were then immersed in the prepared copper sulfate solution. The battery charger was turned on at the 6 volt setting and the electroplating action was continued for 10 hours.

EXAMPLE 7: PREPARATION OF A POROUS FILTER BODY

In substantial accordance with the procedure described in Example 1, and using substantially the same ratios of materials, a ceramic mixture was prepared which contained kaolin, silica, feldspar, soda ash, and gluten. However, instead of using 25 grams of the vital wheat gluten, and 20 grams of such gluten were used.

80.5 grams of the ceramic mixture (dry weight) were mixed with 53 grams of water and stirred for 3 minutes to produce a substantially homogeneous slurry.

An "O-CELL-O" sponge, which was 2.5 inches wide by 4.25 inches long by 0.5 inches thick, was cut into 1.4 inch segments. One segment of the sponge was then compressed and immersed into the slurry; while in the slurry, the compressive force on the sponge was released, thereby saturating the sponge with slurry.

The saturated sponge was then charged to a conventional microwave and subjected to radiation at the high setting for three minutes; during microwave treatment, the sample was rotated with a conventional mechanical microwave rotisserie at a speed of about 6 revolutions per minute.

The microwaved sponge material was then charged to a gas-fired furnace and heated to a temperature of 1170 degrees Celsius over a period of 12 hours. Once the material had reached the 1170 degree Celsius temperature, it was maintained at this temperature for 5 minutes. Thereafter, it was cooled to ambient over a period of 12 hours.

The fired body was sectioned. Visual observation indicated that, although it was lightweight, it had a uniform, form, fine pore distribution.

EXAMPLE 8

The procedure of Example 7 was substantially repeated, with the exception that the slurry was prepared by mixing 80.5 grams of the ceramic mixture with 67 grams of water, and the saturated sponge material was subjected to microwave radiation for 4.5 minutes at the high setting. The fired body of this example had greater porosity than the fired body of Example 7.

EXAMPLE 9

The procedure of Example 8 was substantially repeated, with the exception that the slurry was prepared by mixing 80.5 grams of the ceramic mixture with 75 grams of water, and the saturated sponge material was subjected to microwave radiation for 6.0 minutes at the high setting. The fired body of this example had greater porosity than the fired body of Example 8.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A process for preparing a porous ceramic material, comprising the steps of sequentially:
   (a) providing an organic sponge material which, after being heated to a temperature of 800 degrees Celsius for at least 60 minutes, will have at least 95 weight percent of its content of solid material converted to gas;
   (b) providing a slurry comprised of liquid, gluten, and ceramic material, wherein said slurry is comprised of at least about 60 weight percent of said ceramic material and from about 1 to about 40 weight percent of glutent, by combined weight of ceramic material and gluten, and from about 45 to about 75 weight percent of liquid, by combined weight of liquid, ceramic material, and gluten;
   (c) applying said slurry to said organic sponge so that said organic sponge contains from about 95 to about 100 weight percent of the maximum amount of said slurry it is capable of holding, thereby providing a substantially saturated organic sponge;
   (d) dehydrating said substantially saturated organic sponge so that said sponge contains less than about 5.0 weight percent of said liquid, thereby providing a dehydrated organic sponge; and
   (e) subjecting said dehydrated organic sponge to a temperature of from about 1,100 to about 3,500 degrees Fahrenheit.

2. The process as recited in claim 1, wherein said liquid is water.

3. The process as recited in claim 1, wherein said substantially saturated organic sponge is subjected to microwave radiation prior to the time it is subjected to said temperature of from about 1,100 to about 3,500 degrees Fahrenheit.

4. The process as recited in claim 1, wherein said saturated organic sponge is heated to a temperature of from about 300 to about 450 degrees Fahrenheit for at least about 2 minutes prior to the time it is subjected to said temperature of from about 1,100 to about 3,500 degrees Fahrenheit.

5. The process as recited in claim 1, wherein said saturated organic sponge is hot pressed at a pressure of from about 18 to about 175 pounds per square inch and a temperature of from about 200 to about 600 degrees Fahrenheit prior to the time it is subjected to said temperature of from about 1,100 to about 3,500 degrees Fahrenheit.

6. The process as recited in claim 5, wherein said hot pressing occurs for from about 2 to about 5 minutes.

7. The process as recited in claim 1, wherein said dehydrated organic sponge is subjected to machining prior to the time it is subjected to said temperature of from about 1,100 to about 3,500 degrees Fahrenheit.

8. The process as recited in claim 7, wherein said machining includes the step of grinding said dehydrated organic sponge.

9. The process as recited in claim 7, wherein said machining includes the step of cutting said dehydrated organic sponge.

10. The process as recited in claim 7, wherein said machining includes the step of drilling said dehydrated organic sponge.

11. The process as recited in claim 1, wherein said gluten is vital wheat gluten.

12. The process as recited in claim 1, wherein said gluten is corn gluten.

13. The process as recited in claim 12, wherein said corn gluten is in the form of corn meal.

14. The process as recited in claim 3, wherein said gluten is selected from the group consisting of vital wheat gluten, corn gluten, and mixtures thereof.

15. The process as recited in claim 14, wherein said saturated organic sponge is subjected to microwave radiation until it contains less than about 0.5 weight percent of water.

16. The process as recited in claim 15, wherein said organic sponge consists essentially of polyurethane foam.

17. The process as recited in claim 15, wherein said organic sponge consists essentially of polyvinyl acetate.

* * * * *